United States Patent [19]

Cooper et al.

[11] Patent Number: 5,262,014

[45] Date of Patent: Nov. 16, 1993

[54] PROCESS FOR REMOVING ACETONE FROM A MIXTURE OF ACETONE, METHYL, ACETATE AND METHYL IODIDE

[75] Inventors: Jeremy B. Cooper, West Sussex; John Dixon-Hall; Stephen J. Smith, both of Hull, all of England

[73] Assignee: The British Petroleum Company p.l.c., London, England

[21] Appl. No.: 898,771

[22] Filed: Jun. 12, 1992

[30] Foreign Application Priority Data

Jun. 12, 1991 [GB] United Kingdom ............... 9112623

[51] Int. Cl.$^5$ .................... B01D 3/34; C07C 45/83
[52] U.S. Cl. ........................ 203/53; 203/61; 203/93; 203/94; 203/96; 203/97; 203/98; 203/99; 203/DIG. 19; 203/DIG. 21; 560/248; 568/411; 570/262; 570/263
[58] Field of Search .......... 203/53, 96, 93, DIG. 21, 203/97, 98, 99, DIG. 6, DIG. 19, 94, 61, 14; 568/411; 560/248; 570/262, 263

[56] References Cited

U.S. PATENT DOCUMENTS

| | | | |
|---|---|---|---|
| 2,249,847 | 7/1941 | Murray | 562/892 |
| 2,704,271 | 3/1955 | Harrison et al. | 203/70 |
| 2,710,829 | 6/1955 | Michael | 203/44 |
| 2,878,283 | 3/1959 | Othmer | 562/608 |
| 2,906,675 | 9/1959 | Hall et al. | 203/53 |
| 3,409,513 | 11/1968 | Hamlin et al. | 203/33 |
| 3,531,376 | 9/1970 | Minoda et al. | 203/46 |
| 3,547,783 | 12/1970 | Yamaguchi et al. | 293/99 |
| 3,692,636 | 9/1972 | Huguet | 203/99 |
| 3,738,915 | 6/1973 | Fiore et al. | 203/99 |
| 4,008,131 | 2/1977 | Price | 203/99 |
| 4,252,748 | 2/1981 | Hoch et al. | 203/62 |
| 4,444,624 | 4/1984 | Erpenbach et al. | 203/61 |
| 4,717,454 | 1/1988 | Erpenbach et al. | 203/29 |
| 4,722,769 | 2/1988 | Chan et al. | 203/99 |
| 5,057,192 | 10/1991 | Zoeller et al. | 203/83 |

FOREIGN PATENT DOCUMENTS

| | | |
|---|---|---|
| 0074506 | 3/1983 | European Pat. Off. |
| 0087870 | 9/1983 | European Pat. Off. |
| 0170964 | 12/1986 | European Pat. Off. |
| 0314355 | 5/1989 | European Pat. Off. |
| 61056144A | 3/1986 | Japan . |
| 722390 | 1/1955 | United Kingdom . |
| 740716 | 11/1955 | United Kingdom . |
| 741485 | 12/1955 | United Kingdom . |

Primary Examiner—Virginia Manoharan
Attorney, Agent, or Firm—David J. Untener; Brian L. Mehosky

[57] ABSTRACT

A process for removing acetone from an acetone/methyl acetate/methyl iodide mixture utilizing extractive distillation with water being introduced to the distillation zone above the point of introduction of the mixture and acetic acid being introduced at or above the point of introduction of the mixture. In a preferred embodiment the mixture is subjected to an initial extraction with an aqueous extractant to remove most of the methyl iodide.

The process is particularly applicable to removing acetone by-product in carbonylation processes for the production of acetic anhydride.

13 Claims, 3 Drawing Sheets

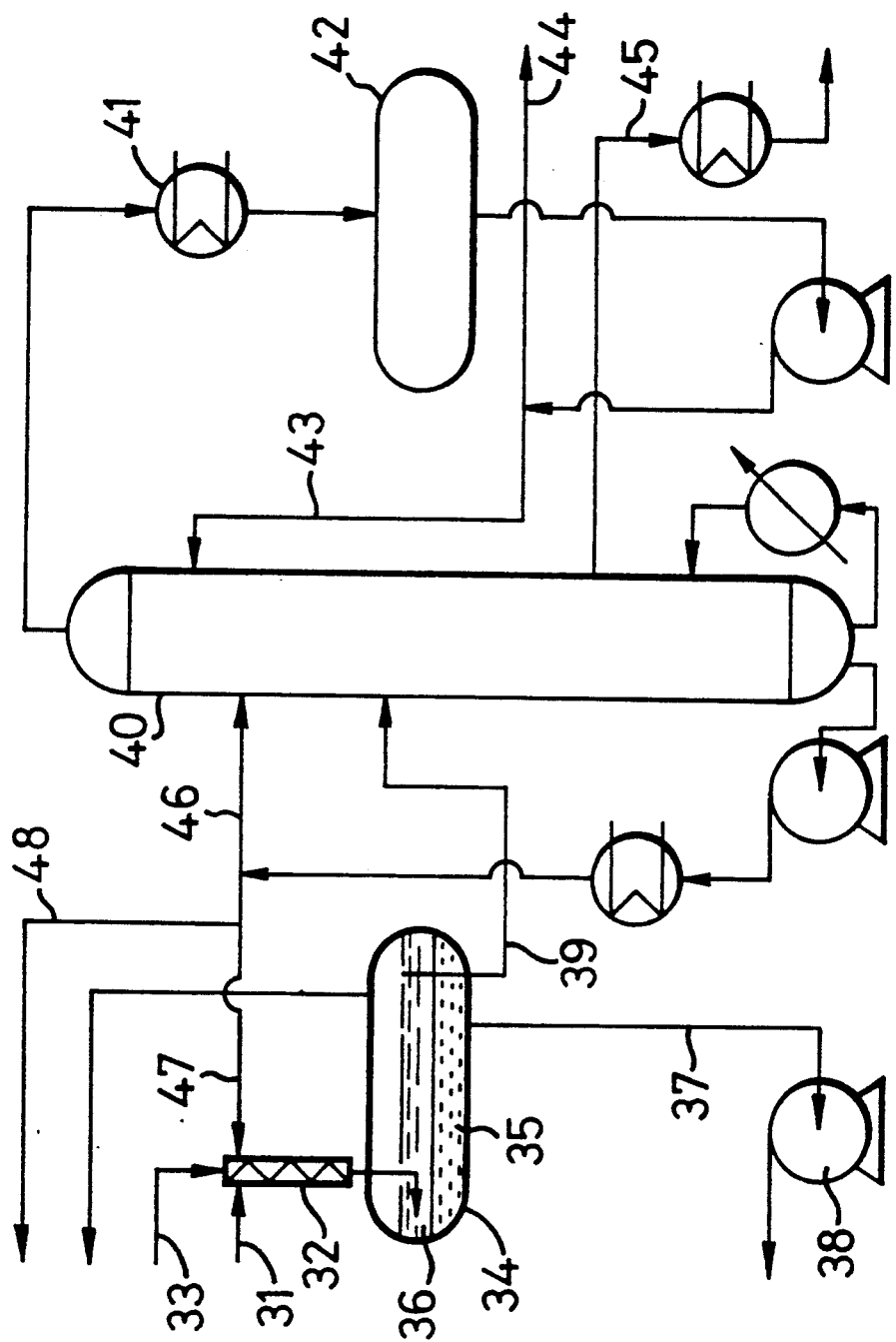

PROCESS FOR REMOVING ACETONE FROM A MIXTURE OF ACETONE, METHYL, ACETATE AND METHYL IODIDE

This invention relates to a separation process for removing acetone from a mixture comprising acetone, methyl acetate and methyl iodide.

In recent years carbonylation processes, in particular rhodium catalysed carbonylation processes, have become industrially important. Typical of such processes are the production of acetic anhydride by carbonylation of methyl acetate and/or dimethyl ether (for example, as described in European patent publication number EP 170964A) and the coproduction of acetic acid and acetic anhydride by the carbonylation of methanol/methyl acetate/water mixtures (for example, as described in European patent publication number EP 87870A).

Acetone is often produced as a by-product of such carbonylation processes. This by-product can build up in process recycle streams comprising methyl acetate and methyl iodide and may lead to further undesirable by-products and/or reduction of the overall process efficiency. Acetone is difficult to separate from methyl acetate because of the formation of an azeotrope.

A known process involving the separation of methyl acetate from acetone is described in UK patent number GB 722390 which describes a process for separating methyl acetate from a mixture of organic compounds containing methyl acetate, propionaldehyde, acetone, methanol and other alcohols (obtained by oxidation of aliphatic hydrocarbons) by subjecting the mixture to an extractive distillation employing water as the extracting agent to obtain an overhead product consisting mainly of methyl acetate and substantially free from propionaldehyde and an aqueous bottom product containing substantially the whole of the propionaldehyde and the bulk of the other components present in the initial mixture. However, GB 722390 is concerned mainly with obtaining methyl acetate substantially free from propionaldehyde rather than separating acetone from methyl acetate and methyl iodide.

Another process for separating acetone from methyl acetate is described in U.S. Pat. No. 2,704,271 which describes azeotropic distillation with n-pentane to produce an acetone/n-pentane azeotrope.

Several processes are also known for removing acetone from mixtures of acetone, methyl acetate and methyl iodide.

Thus, U.S. Pat. No. 4,717,454 describes a process for removing by-product acetone from reaction mixtures obtained by carbonylation of methyl acetate and/or dimethyl ether in which the by-product acetone is subjected to a condensation at temperatures of 50° to 250° C. under pressures of 0.01 to 150 bar so as to obtain predominantly higher-boiling secondary products to be distillatively separated in a successive distillation zone.

Japanese patent publication number J61056144A describes a process for removing acetone from a reaction mixture of a carbonylation process in which a mixture (B) of methyl iodide, acetone and methyl acetate is separated from other high boiling components (C) and mixture (B) is subjected to azeotropic distillation with methanol to produce a methanol/methyl iodide mixture (D) and an acetone/methyl acetate mixture (E). The aceton is separated from the methyl acetate by known methods e.g. azeotropic distillation with n-pentane as in U.S. Pat. No. 2,704,271 followed by extraction with water.

U.S. Pat. No. 4,252,748 describes a process for removing acetone from the volatile constituents of a reaction mixture which is obtained by carbonylation of methyl acetate in the presence of a Group VIII noble metal and methyl iodide, the process comprising: establishing an acetone to methyl iodide molar ratio of at least 1:10 in the mixture of volatile constituents by introducing acetone, methyl iodide and methyl acetate to the carbonylation reaction; fractionally distillating the mixture of volatile components to separate practically all of the methyl iodide and a portion of the acetone and methyl acetate, the quantity of acetone separated corresponding practically to the quantity supplied to the reaction; distilling off the remaining acetone and methyl acetate from the bottoms of the distillation and recovering the acetone from the methyl acetate/acetone-mixture by azeotropic distillation with $C_5$-hydrocarbons (see U.S. Pat. No. 2,704,271) followed by extraction of the acetone/$C_5$-hydrocarbon-mixture with water, and fractionation of the acetone from the water phase.

U.S. Pat. No. 4,444,624 described a process for removing acetone from reaction mixtures originating from the carbonylation of methyl acetate and/or dimethyl etherr in which the reaction mixture or just its low boiler fraction consisting of methyl acetate, methyl iodide and acetone, is subjected wholly or partially to an extractive distillation with acetic acid to distil off pure methyl iodide. The resultant acetone/methyl acetate mixture is said to be separated into its components in art-recognised fashion in a further column with the aid of a $C_5$-hydrocarbon mixture by azeotropic distillation. The distillate is said to be the acetone/$C_5$-hydrocarbon azeotrope and the base product methyl acetate free from hydrocarbons. The acetone/$C_5$-hydrocarbon mixture is said to be separated into its components in known fashion by subjecting it to countercurrent extraction with water, the acetone being removed from the water by stripping. Alternatively, acetone/$C_5$-hydrocarbon azeotrope is said to be separated by extractive distillation with acetic acid with the $C_5$-hydrocarbon as distillate and an acetone/acetic acid mixture as base product, which can be separated into its components by fractional distillation.

European patent publication number EP 0314355A describes a process for removing methyl iodide from a mixture comprising methyl iodide, methyl acetate and optionally acetone, using countercurrent extractive distillation with acetic acid. The overhead fraction from the distillation column has a methyl iodide content greater than that of the methyl iodide/methyl acetate or methyl iodide/methyl acetate/acetone azeotropes. The bottom fraction comprises methyl acetate, acetic acid and optionally acetone. In EP 0314355A, acetic acid is used to break the methyl iodide/methyl acetate and the methyl iodide/methyl acetate/acetone azeotropes, the methyl acetate, and optionally acetone, being removed together from the bottom of the distillation zone with the acetic acid.

In J61056144A; U.S. Pat. Nos. 4,252,748; 4,444,624 and EP 0314355A, methyl iodide is removed from a mixture of acetone, methyl acetate and methyl iodide as a heads distillation product, subsequent processing then being required to separate acetone from the methyl acetate in the remaining mixture.

U.S. Pat. No. 5,057,192 published after the priority date of the present application, describes a process for the removal of acetone from a production system in which acetic anhydride is produced by contacting carbon monoxide with a mixture comprising methyl iodide and methyl acetate and/or dimethyl ether in the presence of a catalyst system and acetic acid by the steps comprising:

(1) obtaining from the production system a low-boiling stream comprising methyl acetate, methyl iodide, acetic acid and acetone;
(2) distilling the stream of Step (1) to obtain:
  (a) an overhead stream comprising methyl acetate, methyl iodide and acetone; and
  (b) an underflow stream comprising methyl acetate, acetone and essentially all of the acetic acid;
(3) extracting the Step (2) (a) stream with water to obtain:
  (a) a methyl iodide phase containing methyl acetate; and
  (b) an aqueous phase containing methyl acetate, methyl iodide and acetone; and
(4) distilling the aqueous phase to obtain:
  (a) a vapour phase comprising methyl acetate, methyl iodide and minor amounts of acetone and water; and
  (b) an aqueous stream containing methyl acetate and acetone.

The process described in U.S. Pat. No. 5,057,192 requires the removal of essentially all of the acetic acid present in the acetone/methyl iodide/methyl acetate stream being processed (step 2, distillation column 12).

There remains a need for a process for removing acetone from a mixture comprising acetone, methyl acetate and methyl iodide.

Thus, according to the present invention there is provided a process for removing acetone from a mixture comprising acetone, methyl acetate and methyl iodide, the process comprising the steps:
(a) introducing a mixture comprising acetone, methyl acetate and methyl iodide into a distillation zone;
(b) introducing water into the distillation zone at one or more points above the point of introduction into the distillation zone of the acetone/methyl acetate/methyl iodide mixture;
(c) introducing acetic acid at one or more points at or above the point of introduction into the distillation zone of the acetone/methyl acetate/methyl iodide mixture;
(d) removing from the distillation zone a heads product stream comprising methyl acetate and methyl iodide; and
(e) removing from the distillation zone water, acetic acid and acetone at one or more points below the introduction point of the acetone/methyl acetate/methyl iodide mixture into the distillation zone.

The process of the present invention does not require the removal of acetic acid if it is present in the acetone/methyl iodide/methyl acetate mixture.

The major portions of acetone, acetic acid and water may be removed together from the base of the distillation zone and the acetone separated therefrom in a second distillation zone. A suitable second distillation column for this separation may, for example, have 18 theoretical (32 actual) separation stages and may operate at atmospheric to 3 barg pressure with a reflux to heads take-off ratio of 0.3:1 to 5:1, a base temperature of 105° to 145° C.

Three figures are provided to illustrate possible configurations of the instant invention. FIG. 1 represents a schematic of a process in which a mixture containing acetone, methyl acetate, acetic acid and methyl iodide is introduced to a distillation column, water is introduced to the distillation column above the mixture introduction point, and acetone withdrawn as a side product stream at a point below the mixture introduction point. FIG. 2 shows in schematic form apparatus for use in a continuous process of the present invention in which acetone is removed from a feed mixture containing acetone, methyl acetate and methyl iodide, together with minor amounts of acetic acid and acetic anhydride, in a distillation column with introduction of aqueous acetic acid solution. FIG. 3 represents in schematic form a continuous process in which a feed mixture of methyl iodide, methyl acetate, acetone is subjected to aqueous extraction prior to distillation. Although the figures, and the specific examples which follow, describe the instant invention in considerable detail, these figures are provided for purposes if illustration only. Many variations and modifications can be made by one skilled in the art without departing from the spirit and scope of the invention. and a heads temperature of 65° to 100° C. This will separate acetone as a heads product and water and acetic acid as a base product. All or part of the water and acetic acid removed from the second distillation zone may be recycled for introduction into the first distillation zone.

Alternatively, the major portion of acetone is preferably removed from the distillation zone at a different point to the major portions of the acetic acid and water. In this embodiment, the major portions of acetic acid and water are removed in a base product stream from the base of the distillation zone and the major portion of acetone is removed, in a side product stream, at a point above the base of the distillation zone and below the introduction point of the mixture into the distillation zone. This has the advantage that all or part of the acetic acid and water removed separately from the distillation zone as base product may be recycled for re-introduction into the distillation zone without further purification. Preferably, the side product stream is removed as a vapour from the distillation zone. The side product stream may also contain some acetic acid, water and methyl acetate and some further purification may be desirable.

In a first embodiment of the present invention the acetone/methyl acetate/methyl iodide mixture may additionally comprise sufficient acetic acid so that additional, separate introduction of acetic acid to the distillation zone is not required. Typically, such a mixture might comprise by weight about 40–60% acetic acid, 30–45% methyl acetate, about 3% acetone and about 3% methyl iodide.

In this first embodiment the ratio of water to acetone/methyl acetate/methyl iodide/acetic acid mixture will depend upon such factors as the composition of the acetone/methyl acetate/methyl iodide/acetic acid mixture, the required compositions of the product streams and the number of separation stages in the distillation zone. Typically, for an acetone/methyl acetate/methyl iodide/acetic acid mixture comprising about 53% by weight acetic acid, the ratio of water to mixture may suitably be about 1:1.5. Increasing the amount of water tends to increase acetone removal. The distillation zone will be operated with a return of liquid reflux to the head of the column at a reflux to heads ratio dependent upon such factors as the required heads stream composition.

A typical configuration of the distillation zone for this first embodiment is a distillation zone having 18 theoretical separation stages with water feed at stage 2 counted from the head; mixture feed at stage 3 counted from the head; heads product take-off of methyl acetate and methyl iodide; side product take-off comprising acetone at stage 8 counted from the head; and base product take-off of water and acetic acid. The side product stream may be removed from the distillation zone as a liquid or vapour, preferably as a vapour. The distillation zone may be operated at any suitable pressure. High pressures result in higher operating temperatures and hence potentially more corrosive conditions. A suitable operating pressure is about 2 barg.

In a second embodiment of the present invention, the mixture may comprise no acetic acid or insufficient acetic acid such that further introduction of acetic acid is required. Typically, such a mixture might comprise by weight about 50–60% methyl iodide, about 35–50% methyl acetate and about 1–2% acetone. In this second embodiment all or part of each of the acetic acid and water may be introduced into the distillation zone separately or together. Preferably, an aqueous acetic acid solution is introduced into the distillation zone above the point of introduction of the mixture. Whether introduced separately or together the ratio by weight, of acetic acid: water should preferably be at least about 50:50, more preferably from about 50:50 to 99:1, even more preferably from about 50:50 to 95:5 and most preferably about 70:30. If the acetone/methyl acetate/methyl iodide mixture also contains acetic acid and water the amounts of acetic acid and water introduced separately may be reduced by an appropriate amount. The ratios of acetic acid and water to acetone/methyl acetate/methyl iodide mixture introduced into the distillation zone in this second embodiment will depend upon such factors as the composition of the acetone/methyl acetate/methyl iodide mixture; the ratio of water and acetic acid streams; the required compositions of the product streams; and the number of theoretical separation stages in the distillation zone. The ratio of reflux to heads product will depend upon such factors as the required heads stream composition. A typical reflux ratio is about 4:1. Typically the distillation zone in this second embodiment has about 40 theoretical stages with an acetic acid/water feed at plate 2 from the head and methyl acetate/methyl iodide/acetone feed at plate 25 from the head. The distillation zone in the second embodiment may be operated at any suitable pressure, for example 3 bara. High pressures result in high operating temperatures and hence potentially more corrosive conditions.

In a third embodiment, the acetone/methyl acetate/methyl iodide mixture may be sufficiently rich in methyl iodide that it may be subjected to an initial aqueous extraction to separate most of the methyl iodide as an organic phase and thus reduce the load on the distillation column. Typically, such a mixture may comprise by weight about 50–60% methyl idode, about 35–50% methyl acetate and about 1–2% acetone.

Thus, according to a third embodiment of the present invention there is provided a process for removing acetone from a mixture comprising acetone, methyl acetate and methyl iodide, the process comprising the steps:

(i) contacting a mixture comprising acetone, methyl acetate and methyl iodide with an aqueous extractant to form an aqueous phase comprising at least part of the acetone and methyl acetate and some methyl iodide from the acetone/methyl acetate/methyl iodide mixture, and an organic phase comprising at least part of the methyl iodide from the acetone/methyl acetate/methyl iodide mixture;

(ii) separating the aqueous and organic phases;

(iii) introducing the aqueous phase into a distillation zone;

(iv) introducing water into the distillation zone at one or more points above the point of introduction into the distillation zone of the aqueous phase;

(v) introducing acetic acid into the distillation zone at one or more points at or above the point of introduction into the distillation zone of the aqueous phase;

(vi) removing from the distillation zone a heads product stream comprising methyl acetate and methyl iodide; and (vi) removing from the distillation zone water, acetic acid and acetone at one or more points below the introduction point of the aqueous phase into the distillation zone.

This third embodiment of the present invention has the advantage that the aqueous extraction reduces the load on the distillation column.

In this third embodiment, the acetone/methyl acetate/methyl iodide must be immiscible with the aqueous extractant. Therefore, the process of the present invention is particularly suitable for mixtures which are rich in methyl iodide. The mixture may also contain other components in particular such as acetic acid.

In the third embodiment, one or more extraction/separation steps (i) and (ii) may be used, for example as in a multi-stage, liquid-liquid extraction process. The number of extraction/separation stages will depend upon, amongst other things, the composition of the acetone/methyl acetate/methyl iodide mixture; the composition of the aqueous extractant and the required compositions of the organic and aqueous phases. The extraction/separation steps (i) and (ii) may be operated as a batch or continuous process, preferably as a continuous process. The extraction/separation steps (i) and (ii) may be operated continuously in a counter-flow multistage extraction column, for example a packed tower or rotating disk extraction column (Kuhni column), or may be operated continuously with a single separation stage, for example by co-feeding an acetone/methyl acetate/methyl iodide mixture with the aqueous extractant through a mixer to a decanter where the organic and aqueous phases are separated. The extraction/separation steps (i) and (ii) may be performed at a temperature between 0° C. and 50° C., preferably between 10° C. and 40° C. and at a pressure of about 1 bara to 4 bara. The ratio of aqueous extractant to acetone/methyl acetate/methyl iodide mixture will depend upon parameters such as the number of extraction/separation steps, the compositions of the aqueous extractant and acetone/methyl acetate/methyl iodide mixture and the required compositions of the aqueous and organic phases. A typical ratio of mixture: aqueous extractant is 1:1.06 but higher ratios may be used for example up to about 1:5. The aqueous extractant may comprise water alone or with minor amounts of other components, for example methyl iodide, methyl acetate and/or acetic acid. The aqueous extractant may contain acetic acid, suitably at about 10 to 20% by weight. The acetone/methyl acetate/methyl iodide mixture may also contain acetic acid. Preferably, at least one of the aqueous extractant and acetone/methyl acetate/methyl iodide mixture contains acetic acid.

As regards the distillation steps (iii) to (iv) all or part of each of the water and acetic acid may be introduced into the distillation zone separately or together. Preferably, an aqueous acetic acid solution is introduced into the distillation zone above the point of introduction of the aqueous phase. Water and optionally acetic acid will also be introduced into the distillation zone in the aqueous phase. The aqueous phase will also contain some methyl acetate and methyl iodide from the original acetone/methyl acetate/methyl iodide mixture. Whether introduced separately or together the total weight ratio of acetic acid: water including acetic acid and water introduced in the aqueous phase may be in the range 99:1 to 1:99. It is preferred however, that the ratio is 1:1 to 1:99, preferably about 1:1 to 1:19, more preferably about 1:4. The ratios of aqueous phase: aqueous acetic acid solution introduced into the distillation zone will depend upon such factors as the composition of the aqueous phase; the required compositions of the product streams; and the number of theoretical separation stages in the distillation zone. A typical value is in the range 1:10 to 10:1, preferably about 3:1 by weight.

The ratio of reflux to heads product of the distillation zone in steps (iii) to (vi) will depend upon such factors as the required heads stream composition, and may suitably be in the range 0.3:1 to 10:1. Typically, the distillation zone in steps (iii) to (vi) may have 10 to 20 theoretical separation stages and feed points for the aqueous phase and water/acetic acid at plates 2 to 10 counted from the head. Typically for an 18 stage column the aqueous phase feed point may be at stage 15 from the base, the acetic acid/water feed point may be at stage 16 from the base and a vapour side take-off may be at stage 6 from the base. The distillation zone may be operated at any suitable pressure. High pressures result in high operating temperatures and hence potentially more corrosive conditions.

Whether removed from the distillation zone separately from the acetone or separated subsequently in a second distillation zone, all or part of the water and acetic acid separated from the acetone may be recycled for re-introduction into the distillation zone and/or recycled to the extraction/separation process, if present, for use as part of the aqueous extractant.

In preferred embodiments of the present invention, the mixtuere of acetone, methyl acetate and methyl iodide may be recovered as a light ends fraction comprising acetone, methyl acetate and methyl iodide from a reaction mixture produced by the carbonylation of methyl acetate and/or dimethyl ether in the presence of free or combined metallic carbonylation catalyst, a catalyst promoter and alkyl halide. In these embodiments, the organic phase from the extraction/separation, if present, and the heads product from the distillation zone are recycled to the carbonylation reaction zone. Any of the known metallic carbonylation catalysts may be employed for the carbonylation reaction. Suitable metals include the metals of Group VIII of the Periodic Table of the Elements namely iron, cobalt, nickel, ruthenium, rhodium, palladium, osmium, iridium and platinum. Preferred Group VIII metal catalysts are iridium, osmium, platinum, palladium, rhodium and ruthenium. Particularly preferred is rhodium. It is preferred to employ the metal in the form of a soluble compound such as a salt or a complex of the metal, for example a carbonyl complex. As carbonylation catalyst promoter there is used halogen in free or combined form. The catalyst promoter may comprise quaternary organonitrogen compounds, for example N,N-dimethyl imidazolium iodide or N-methyl pyridinium iiodide; quaternary organo-phosphorous compounds, for example tetrabutyl phosphonium iodide; and/or alkali metal salts, for example lithium iodide. The alkyl halide is preferably methyl iodide. Suitable carbonylation reaction conditions are described in European patent application publication number EP 0087870A which is hereby incorporated by reference.

In addition to the catalyst, promoter and alkyl iodide the reaction mixture will generally contain acetic acid, acetic anhydride, ethylidene diacetate, and methyl acetate. The light ends fraction may be separated from the reaction mixture by distillation, preferably fractional distillation.

It will be appreciated by those skilled in the art, that in an integrated carbonylation process there are several light ends fraction process recycle streams which comprise acetone, methyl acetate and methyl iodide which may be used in the process of the present invention thereby to prevent the build up of acetone in the carbonylation reaction mixture. Thus is one embodiment, the carbonylation reaction mixture, which is at elevated pressure and temperature, is passed from a reaction zone through a flash zone where its pressure and temperature are reduced. High boiling and involatile catalyst components are recycled to the carbonylation reaction zone from the base of the flash zone. A mixture of light ends fraction together with acetic acid and acetic anhydride carbonylation products is taken overhead from the flash zone. Some or all of the light ends fraction is separated from the carbonylation products by one or more distillation steps for use in the process of the present invention.

BRIEF DESCRIPTION OF THE DRAWINGS

The invention will now be illusttrated by way of example only and with reference to the drawings in which FIG. 2 represents distillation apparatus for use in the second embodiment of the present invention and FIG. 3 represents in schematic form apparatus for use in the third embodiment of the present invention.

DESCRIPTION OF THE PREFERRED EMBODIMENTS

Figure 1:
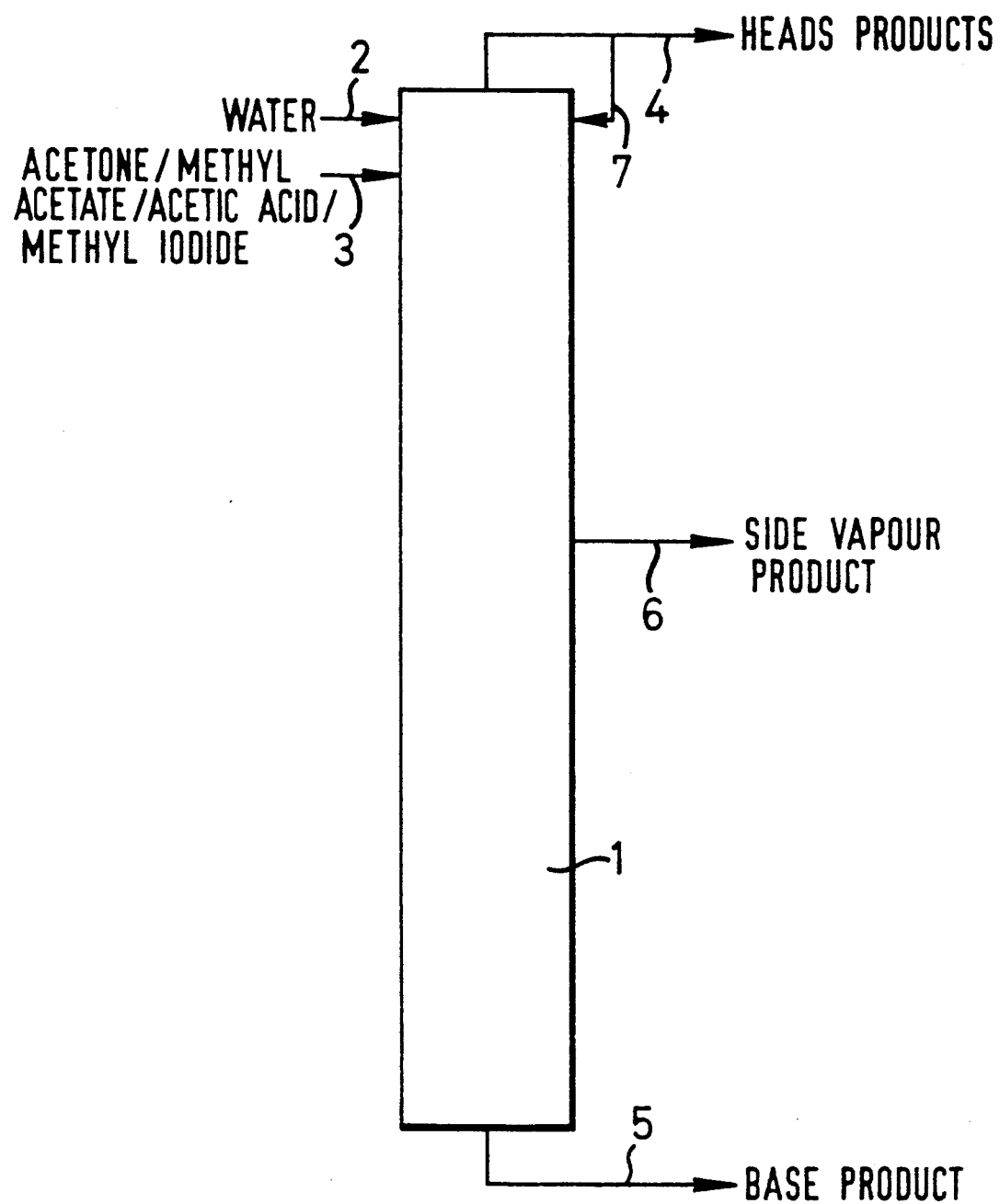
FIG. 1 represents in schematic form distillation apparatus for use in the first embodiment of the present invention.

Referring to FIG. 1 which shows a distillation column for use according to the first embodiment of the present invention to remove acetone from a mixture comprising methyl iodide, methyl acetate, acetone and acetic acid. A distillation column (1) is provided with 18 theoretical separation stages (not shown) numbered from the head. The column is provided with a supply line (2) for water at stage 2 and a supply line (3) for acetone/methyl acetate/methyl iodide/acetic acid at stage 3. A heads product line (4), base product line (5) and side product line (6) at stage 8, are provided. A reflux return (7) is provided to the head of the column.

In operation, a mixture comprising acetone, methyl acetate, methyl iodide and acetic acid is introduced to the distillation column along line (3) and water is introduced along line (2) to the distillation column above the introduction point of the mixture. The mixture is sufficiently rich in acetic acid that further separate introduction of acetic acid is not required. A head product is removed along line (4) from the head of the column and reflux is returned along line (7). The heads product comprises major portions of the methyl acetate and methyl iodide introduced into the distillation zone in the mixture. A base product comprising water and acetic acid introduced into the distillation column is removed along line (5). A side vapour product comprising acetone is removed from stage 8 along line (6).

The operation at 3 bar head pressure of such a distillation column having 18 theoretical separation stages with water feed at stage 2 and mixture feed at stage 3 counted from the head was simulated using an ASPEN RADFRAC BLOCK computer model.

The feed composition by weight was methyl acetate 41.1%; acetone 2.8%, acetic acid 53% and methyl iodide 3.1%. The results are given in Tables 1 and 2 for different water feed rates and different positions of the side take-off. Acetone removal is expressed as acetone in side take-off divided by acetone in feed mixture expressed as a percentage.

From a study of the results in the Tables, the following conclusions may be drawn. Firstly, water is essential for removal of acetone, see comparative experiment CT1. Also, the results show that the amount of acetone removed and the acid concentration in the side product can be changed by changing the amount of water feed and the position of the side product take-off. Moving the side product take-off up the column reduces the amount of acid left in the side product stream but also reduces acetone removal. Therefore, there will be a preferred configuration depending upon the application required.

Figure 2:
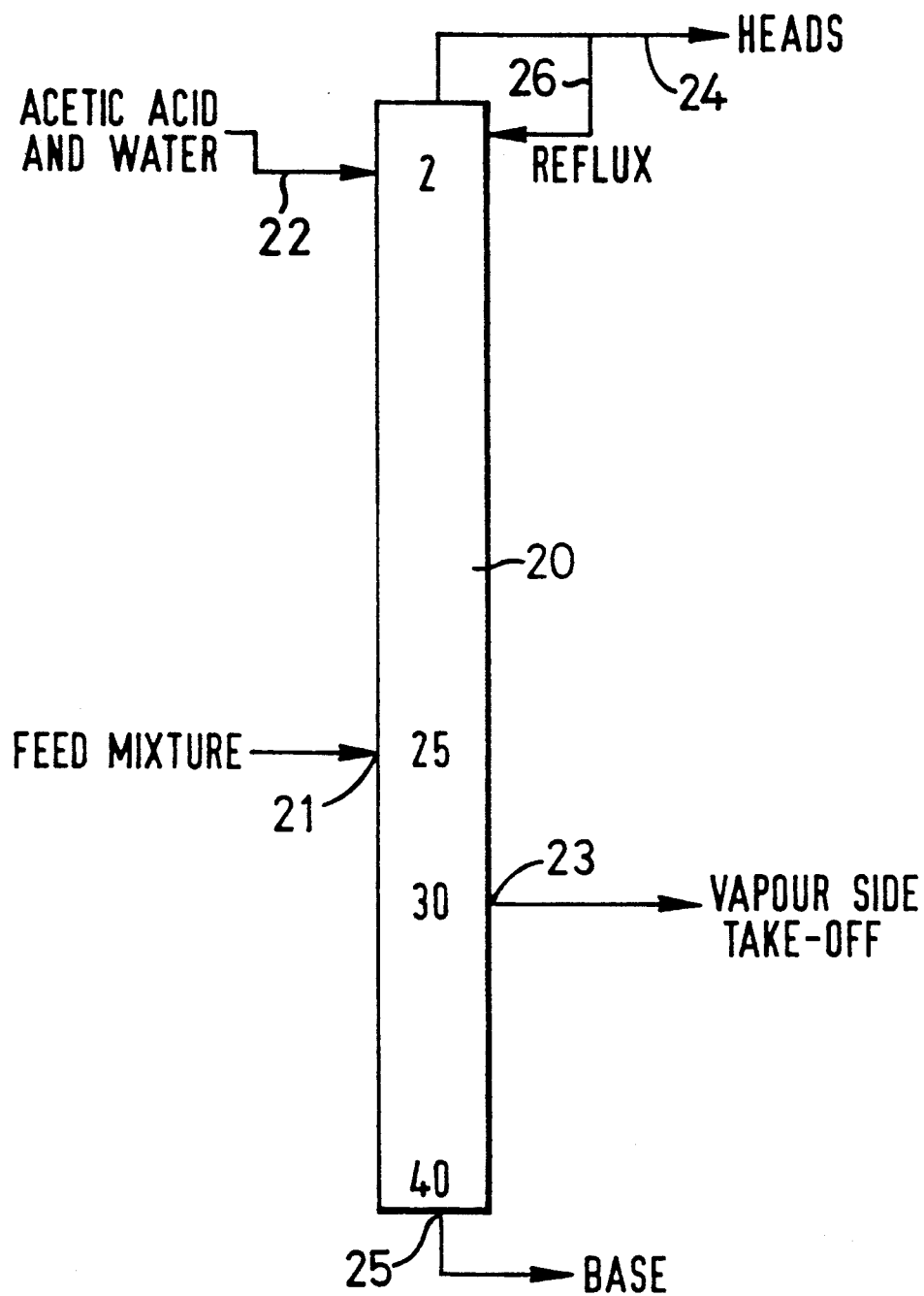

Using a distillation column such as shown in FIG. 1 it is expected that acetone may be continuously removed from a integrated carbonylation process to prevent its build up.

ing acetone, methyl acetate and methyl iodide together with minor amounts of acetic acid and acetic anhydride, in a distillation column with introduction of aqueous acetic acid solution. Referring to FIG. 2, a distillation column (20) having 40 theoretical separation stages is provided with a feed point (21) at plate 25 (numbered from the head) for acetone/methyl acetate/methyl iodide mixture; a feed point (22) at plate 2 for acetic acid/water solution; a vapour side product take-off point (23) at plate 30; reflux return (26) to the column head and heads (24) and base (25) product take-off points. In use, the acetone/methyl acetate/methyl iodide mixture is introduced into the distillation column (20) at feed point (21) and acetic acid/water solution is introduced at feed point (22). Heads product comprising methyl acetate and methyl iodide is taken at take-off point (24) with reflux being returned to the head of the column. Base product comprising acetic acid and water is taken at base take-off point (25) and a vapour side product comprising acetone, acetic acid and water with some methyl acetate is taken at take-off point (23). Using an ASPEN RADFRAC BLOCK computer model of the distillation column shown in FIG. 2 the removal of acetone from a mixture comprising, by weight 1.0% acetone, 35% methyl acetate, 60% methyl iodide, 4% acetic acid and 0.1% acetic anhydride at a feed rate of 4071 parts/hour was simulated using different acid/water feeds to the column operating at 3 bara head pressure; and with a reflux: heads product ratio of 4:1. The results are shown in Tables 3 and 4. In the Tables acetone removal is defined as the percentage of acetone in the feed which is removed in the side vapour take-off stream. From Tables 3 and 4 it will be seen that the weight ratio of acetic acid to water is preferably at least 50:50. With this particular acetone/methyl acetate/methyl iodide mixture and this distillation column, the largest acetone separation was achieved with a weight ratio of acetic

TABLE 1

| Expt No | Position of side product take off (stage from head) | Flow Rates (parts/hour) | | | | | Acetone Removal % |
|---|---|---|---|---|---|---|---|
| | | water | mixture | Heads | Base product | Side Product | |
| 2 | 12 | 1000 | 1516 | 692 | 825 | 1000 | 98.1 |
| 3 | 12 | 500 | 1516 | 697 | 320 | 1000 | 96.0 |
| 4 | 10 | 500 | 1516 | 700 | 813 | 504 | 95.4 |
| 5 | 8 | 500 | 1516 | 700 | 1027 | 290 | 91.9 |
| 6 | 7 | 500 | 1516 | 700 | 1095 | 222 | 86.5 |
| 7 | 5 | 500 | 1516 | 700 | 1193 | 123 | 60.8 |
| 8 | 8 | 500 | 1516 | 700 | 1000 | 1000 | 91.1 |
| CT1 | 12 | 0 | 1516 | 707 | 709 | 100 | 1.2 |

TABLE 2

| | COMPOSITIONS (wt %) | | | | | | | | | |
|---|---|---|---|---|---|---|---|---|---|---|
| | Heads Product Stream | | | | Base Product Stream | | Side Product Stream | | | |
| Expt No | Methyl Acetate | Acetone | Water | Methyl Iodide | Acetic Acid | Water | Acetone | Acetic Acid | Methyl Acetate | Water |
| 2 | 87.5 | 0.1 | 5.8 | 6.6 | 67 | 33 | 4.2 | 25.3 | 1.8 | 68.5 |
| 3 | 86.7 | 0.24 | 6.5 | 6.5 | 99.2 | 0.8 | 4.1 | 48.7 | 1.9 | 45.2 |
| 4 | 86.7 | 0.27 | 6.4 | 6.5 | 80.7 | 19.3 | 8.0 | 29.3 | 3.2 | 59.1 |
| 5 | 86.5 | 0.49 | 6.4 | 6.5 | 70.9 | 29.1 | 13.4 | 26.2 | 6.1 | 53.8 |
| 6 | 86.3 | 0.81 | 6.4 | 6.5 | 68.5 | 31.5 | 16.6 | 24.2 | 8.9 | 49.7 |
| 7 | 84.9 | 2.4 | 6.2 | 6.5 | 65 | 35 | 20.9 | 17.4 | 23.7 | 36.6 |
| 8 | 86.6 | 0.47 | 6.4 | 6.5 | 52.7 | 41.6 | 3.9 | 52.7 | 1.7 | 41.6 |
| CT1 | 87.4 | 5.9 | 0 | 6.4 | 99.8 | 0 | 0.5 | 94.8 | 4.6 | 0 |

The second embodiment of the invention will now be described by way of example only and with reference to FIG. 2 which shows in schematic form, apparatus for use in a continuous process of the present invention in which acetone is removed from a feed mixture comprising acid: water of 70:30. Experiment 25 is a comparative simulation using acetic acid alone and shows that the acetone removal is less than for the other experiments which use acetic acid and water.

A further series of simulations was performed for the same column configuration and feed mixture. The flow rates were fixed as follows: acetic acid/water solution 1500 parts per hour; feed mixture 4071 parts per hour; heads product 4064 parts per hour; base product 12649 parts per hour and side take-off 2358 parts per hour. The ratio of acid:water in the acetic acid/water feed solution was varied and the acetone recovery calculated. The results, shown in Table 5 show that for this column configuration, as the ratio of acid:water increases so does the acetone recovery.

Using a distillation column such as shown in FIG. 2 it is expected that acetone may be continuously removed from an integrated carbonylation process to prevent its build up. The heads product comprising methyl iodide and methyl acetate may be recycled to the carbonylation process. The base product may be used without further purification as part of the acetic acid and water solution feed to the distillation column. The acetone in the side vapour take-off may be further separated from the acetic acid and water by known processes if required.

light ends fraction are intimately contacted and mixed as they pass through the in-line mixer (32). The mixed aqueous extractant and light ends fraction pass into a decanter (34) where they separate into an organic phase (35) and a aqueous phase (36). The organic phase (35), being rich in methyl iodide, is the lower phase in the decanter (34) and is returned to the integrated carbonylation process via line (37) and pump (38). The upper, aqueous phase (36) comprising acetone, water, methyl iodide, methyl acetate and acetic acid overflow from the decanter (34) and passes along line (39) to distillation column (40).

A process stream comprising acetic acid and water is passed along line (46) and introduced into the distillation column at a point above the introduction point of the aqueous phase.

In the distillation column, the methyl iodide and methyl acetate (heads product stream) are separated from the acetone (side product stream) and water and acetic acid (base product stream).

Vapour comprising methyl iodide and methyl acetate from the head of the distillation column (40) passes

TABLE 3

| | | Separation of Acetone | | | | | |
|---|---|---|---|---|---|---|---|
| Expt. No. | Acetic acid/ water solution Feed Rate parts/hour | Solution Composition (weight %) | | Flow Rates (parts/hour) | | | Acetone Removal (%) |
| | | Acetic Acid | Water | Side Vapour | Base | Heads | |
| 10 | 20000 | 50 | 50 | 4838 | 15170 | 4064 | 95.97 |
| 22 | 20000 | 70 | 30 | 3494 | 16425 | 4064 | 99.21 |
| 20 | 20000 | 85 | 15 | 2914 | 16994 | 4064 | 99.19 |
| 26 | 15000 | 70 | 30 | 2357 | 1258 | 4064 | 99.39 |
| CT25 | 20000 | 100 | 0 | 1464 | 18451 | 4063 | 80.84 |

TABLE 4

| | STREAM COMPOSITIONS (Weight %) | | | | | | | | | |
|---|---|---|---|---|---|---|---|---|---|---|
| | Heads Product Stream | | | | | Base Product Strem | | Side Vapour Product | | |
| Expt. No. | Methyl Acetate | Methyl Iodide | Acetone | Water | Acetic Acid | Acetic Acid | Water | Acetone | Acetic Acid | Methyl Acetate | Water |
| 10 | 35.1 | 60 | 0 | 3.8 | 1.1 | 55.9 | 44.1 | 0.81 | 34 | 0.08 | 65 |
| 22 | 33.6 | 60 | 0 | 4.0 | 2.3 | 75.1 | 24.9 | 1.16 | 48 | 1.63 | 49 |
| 20 | 31.1 | 60 | 0 | 4.0 | 4.8 | 89.2 | 10.8 | 1.39 | 60 | 5.36 | 34 |
| 26 | 34.3 | 60 | 0 | 3.8 | 1.9 | 75.1 | 24.9 | 1.72 | 47 | 1.32 | 50 |
| CT25 | 24.6 | 60 | 0 | 0 | 15.3 | 100 | 0 | 2.25 | 70 | 27 | 0 |

TABLE 5

| Run No. | Ratio Acetic acid:water | Acetone Recovery (%) |
|---|---|---|
| 2E1 | 50:50 | 92.4 |
| 2E2 | 13.5:1.5 | 99.2 |
| 2E3 | 4.5:10.5 | 88.9 |
| 2E4 | 3:12 | 83.3 |
| 2E6 | 1.5:13.5 | 84.3 |
| 2E6 | 6:9 | 92.5 |
| 2E7 | 0.75:14.25 | 73.3 |

FIG. 3 represents in schematic form, a flow sheet for a continuous process according to the third embodiment of the present invention in which a methyl iodide/methyl/acetate/acetone mixture is subjected to aqueous extraction prior to distillation. Referring to the apparatus in FIG. 3, in use water, as part of the aqueous extractant is passed along line (31) to an in-line mixer (32). A light ends fraction recovered from a reaction mixture in an integrated carbonylation process (not shown), is passed along line (33) to the mixer (32). The light ends faction comprises a mixture of acetone, methyl iodide, methyl acetate and acetic acid and other carbonylation products. The aqueous extractant and through condenser (41) to reflux drum (42) from which part is returned as reflux to the column along line (43) and part is returned to the integrated carbonylation process along line (44).

Acetone together with some water and acetic acid is taken as a vapour side product stream from the column (40) along line (45).

Part of the base take-off from the distillation column (40) is passed along line (46) and hence back to column (40) as the water/acetic acid feed to the column to aid separation of methyl acetate from acetone, and part is passed along line (47) to the in-line mixer (32) as part of the aqueous extractant to the extraction/separation stage. A small bleed of base take-off is removed along line (48) to prevent build-up of acetic acid.

Based upon ASPEN RADFRAC BLOCK computer modelling of the system shown in FIG. 3, it is expected that continuous operation of this process will allow for removal of acetone from the light ends fraction and hence prevent its build-up in the integrated carbonylation process. The following process conditions may be used:

| | weight % |
|---|---|
| Light ends fraction | |
| Methyl iodide | 60 |
| Methyl acetate | 35 |
| Acetic acid | 4 |
| Acetone | 1 |
| Extraction/separation stage | |
| Ratio of light ends:water:water/acetic acid from column base = 1:0.06:1 (by weight) | |
| Distillation column | |

| Aqueous phase feed | |
|---|---|
| Acetone | 0.46 |
| Methyl iodide | 4.4 |
| Methyl acetate | 9.8 |
| Acetic acid | 15.9 |
| Water | 69.4 |
| Side vapour product stream | |
| Acetone | 14.4 |
| Water | 17.5 |
| Acetic acid | 11.3 |
| Methyl acetate | 2 |
| Heads product stream | |
| Methyl iodide | 29 |
| Methyl acetate | 65 |
| Acetone | 0.4 |
| Water | 5 |
| Base Product stream | |
| Acetic acid | 19 |
| Water | 81 |

Heads: reflux ratio = 5:1.
Weight ratio of aqueous phase:water/acetic acid = 3:1.
Weight ratios of heads product:side product:base product = 1:0.19:7.7
Column pressure = 4 bara
Number of distillation stages = 18 (theoretical)
Aqueous phase feed at stage 15 from base
Water/acetic acid feed at stage 16 from base.
Vapour product take-off at stage 6 from base.

EXTRACTION/SEPARATION PROCESS

The extraction/separation process step of the third embodiment of the present invention was assessed separately in several experiments.

A mixture of acetone, methyl iodide and methyl acetate obtained as a light ends fraction from an integrated carbonylation process was subject to a series of extraction/separation tests using water as aqueous extractant. The composition of this mixture is given in Table 6.

TABLE 6

| Composition of Light Ends Fraction | |
|---|---|
| Component | Composition % w/w |
| Water | 0.007 |
| Methyl Iodide | 49.7 |
| Acetone | 2.0 |
| Methyl Acetate | 46.6 |
| Acetic Acid | 1.2 |

TABLE 7

Extraction Experiments: Feed and Product Weights

| | Weights of Feeds | | | Weight of Separated Phases | | |
|---|---|---|---|---|---|---|
| Experiment Number | Water g | Light Ends Fraction g | Ratios of Water: Light Ends Fraction (Weight/Weight) | Aqueous Phase g | Organic Phase g | Mass Accountability % |
| 101 | 50.0327 | 5.3555 | 9.34:1 | 52.7792 | 1.3715 | 97.8 |
| 102 | 39.7261 | 10.7816 | 3.68:1 | 43.9503 | 5.7160 | 98.3 |
| 103 | 25.5252 | 25.4509 | 1:0.997 | 29.7613 | 20.3008 | 98.2 |
| 104 | 10.0812 | 40.3198 | 1:4.0 | 8.8882 | 40.2207 | 97.4 |
| 105 | 4.9562 | 50.3199 | 1:10.15 | 4.4879 | 49.7317 | 98.1 |
| 106*(1) | 25.2145 | 25.0424 | 1:0.993 | 38.2344 | 16.0377 | 97.7 |
| 107(2) | 40.0900 | 49.3800 | 1:1.23 | 50.5300 | 48.9300 | 99.3 |
| 108(3) | 30.0500 | 49.3900 | 1:1.64 | 41.8100 | 57.6300 | 99.4 |
| 109a | 10.0397 | 20.3029 | | 13.6256 | 16.2926 | 98.6 |
| 109b | 10.3104 | | 1:0.998 | 16.3471 | 8.7310 | 94.3 |

(1) plus 5.2779 g of glacial acetic acid
(2) plus 10.67 g of glacial acetic acid
(3) plus 20.64 g of glacial acetic acid In each experiment, predetermined quantities of the light ends fraction and water were mixed in a 100 ml separating funnel which was stopped and vigorously shaken to ensure intimate contact. The funnel was then left to stand for up to 2 hours to allow aqueous and organic phases to separate. The phases were then drawn off, weighed and analysed.

Experiments 101 to 109 were performed at ambient temperature (about 20° C.).

In Experiments 106–108 glacial acetic acid was added.

Experiment 109 was a two stage extraction/separation in which the organic phase for the first extraction/separation was further extracted with an equal quantity of water to give an overall volume ratio of water to light ends fraction of 1:1.

The results are shown in Table 7.

Table 8 shows the amount of water in the combined feed to these extraction/separations and the acetone extracted (calculated using analysis of the light ends fraction and organic phase only).

TABLE 8

| Acetone Extraction | | |
|---|---|---|
| Experiment Number | Water Used (Weight % of Total Feed) | Acetone Extracted (%) |
| 101 | 90.3 | 97.5 |
| 102 | 78.7 | 89.4 |
| 103 | 50.1 | 60.1 |
| 104 | 20.0 | 15.2 |
| 105 | 9.0 | 6.1 |
| 106 | 45.5 | 71.2 |
| 107 | 44.8 | 49.0 |
| 108 | 37.8 | 53.0 |
| 109 | 50.1 | 80.6 |

The results, show that increasing water feed to the process increases acetone removal into the aqueous phase.

The results also show the benefits of acetic acid in the extraction/separation process steps and that a two stage extraction/separation is better than a single stage process.

Further experiments were performed at 10° C. and 35° C. but these did not indicate a significant temperature effect over that temperature range.

We claim:

1. A process for removing acetone from a mixture comprising acetone, methyl acetate and methyl iodide, the process comprising the steps:
   (a) introducing a mixture comprising acetone, methyl acetate and methyl iodide into a distillation zone;
   (b) introducing water into the distillation zone at one or more points above the point of introduction into the distillation zone of the acetone, methyl acetate, methyl iodide mixture;
   (c) introducing acetic acid at one or more points at or above the point of introduction into the distillation zone of the acetone, methyl acetate, methyl iodide mixture;
   (d) removing from the distillation zone a heads product stream comprising methyl acetate and methyl iodide; and
   (e) removing from the distillation zone water, acetic acid and acetone at one or more points below the introduction point of the acetone, methyl acetate, methyl iodide mixture into the distillation zone.

2. A process as claimed in claim 1 in which the acetone is removed from the distillation zone at a different point to the major portion of the acetic acid and water.

3. A process as claimed in claim 2 in which at least part of the acetic acid and water removed from the distillation zone is re-introduced to the distillation zone.

4. A process as claimed in claim 1 in which the acetone, methyl acetate, methyl iodide mixture additionally comprises acetic acid.

5. A process as claimed in claim 4 in which the acetone, methyl acetate, methyl iodide, acetic acid mixture comprises about 40-60% acetic acid.

6. A process as claimed in claim 1 in which an aqueous acetic acid solution is introduced to the distillation column at a point above the point of introduction of the acetone, methyl acetate, methyl iodide mixture.

7. A process as claimed in claim 6 in which the ratio by weight of acetic acid: water introduced to the distillation zone is at least 50:50.

8. A process as claimed in claim 1 in which a major portion of acetone of said mixture is removed from said distillation zone at a point below the introduction point of said mixture into said distillation zone.

9. A process for removing acetone from a mixture comprising acetone, methyl acetate and methyl iodide which comprises the steps:
   (i) contacting a mixture comprising acetone, methyl acetate and methyl iodide with an aqueous extract to form an aqueous phase comprising at least part of the acetone and methyl acetate and some methyl iodide from the acetone, methyl acetate, methyl iodide mixture, and an organic phase comprising at least part of the methyl iodide from the acetone, methyl acetate, methyl iodide mixture;
   (ii) separating the aqueous and organic phases;
   (iii) introducing the aqueous phase into a distillation zone;
   (iv) introducing water into the distillation zone at one or more points above the point of introduction into the distillation zone of the aqueous phase;
   (v) introducing acetic acid into the distillation zone at one or more points at or above the point of introduction into the distillation zone of the aqueous phase;
   (vi) removing from the distillation zone a heads product stream comprising methyl acetate and methyl iodide;
   (vii) removing from the distillation zone water, acetic acid, and acetone at one or more points below the introduction point of the aqueous phase into the distillation zone.

10. A process as claimed in claim 9 or in which an aqueous acetic acid solution is introduced into the distillation zone above the point of introduction of the aqueous phase.

11. A process as claimed in claim 9 in which at least one of the aqueous extractant and acetone, methyl acetate, methyl iodide mixture contains acetic acid.

12. A process as claimed in claim 9 in which acetone is removed from the distillation zone at a different point to the major portion of the acetic acid and water.

13. A process as claimed in claim 9 in which at least part of the acetic acid and water removed from the distillation zone is re-introduced to the distillation zone.

* * * * *